United States Patent [19]

Schönafinger et al.

[11] Patent Number: 5,120,732

[45] Date of Patent: Jun. 9, 1992

[54] SUBSTITUTED 3-AMINOSYNDONE IMINES, A PROCESS FOR THEIR PREPARATION AND THEIR USE

[75] Inventors: Karl Schönafinger, Alzenau; Rudi Beyerle, Frankfurt; Helmut Bohn, Schöneck; Melitta Just, Nidderau, all of Fed. Rep. of Germany

[73] Assignee: Cassella Aktiengesellschaft, Fed. Rep. of Germany

[21] Appl. No.: 575,388

[22] Filed: Aug. 29, 1990

Related U.S. Application Data

[63] Continuation-in-part of Ser. No. 349,236, May 9, 1989, abandoned.

[30] Foreign Application Priority Data

| | | |
|---|---|---|
| Jun. 14, 1988 [DE] | Fed. Rep. of Germany | 3820210 |
| Nov. 30, 1989 [DE] | Fed. Rep. of Germany | 3939515 |
| Nov. 30, 1989 [DE] | Fed. Rep. of Germany | 3939550 |
| May 13, 1990 [DE] | Fed. Rep. of Germany | 4015236 |
| Jun. 25, 1990 [EP] | European Pat. Off. | 90112002.2 |

[51] Int. Cl.$^5$ ............... A61K 31/38; A61K 31/44; A61K 31/495; C07D 417/02
[52] U.S. Cl. ............... 514/236.2; 514/227.8; 514/255; 514/319; 514/325; 514/326; 514/364; 544/60; 544/138; 544/367; 546/195; 546/203; 546/209; 548/125
[58] Field of Search ............... 548/125; 546/195, 203, 546/209; 544/60, 138, 367; 514/227.8, 236.2, 255, 326, 364, 319, 325

[56] References Cited

U.S. PATENT DOCUMENTS 4,436,743 3/1984 Schönafinger et al. ............... 548/125
4,551,454 11/1985 Schönafinger et al. ............... 548/125

OTHER PUBLICATIONS

The Merck Index, 10th Ed.; 6087 (1983).

Primary Examiner—Johann Richter
Attorney, Agent, or Firm—Perman & Green

[57] ABSTRACT

Substituted 3-aminosydnone imines of the formula I

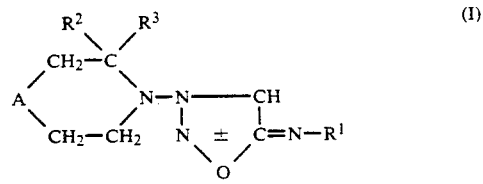

and their pharmacologically acceptable acid addition salts, in which
A denotes, for example, $-CH_2-$,
$R^1$ denotes hydrogen or the radical $-COR^5$,
$R^2$, $R^3$ denote alkyl having 1 to 4 C atoms,
$R^5$ denotes, for example, an aliphatic radical having 1 to 4 C atoms, and methods for preparing such compounds by cyclization of a compound of the formula II

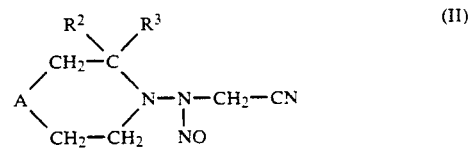

and if desired subsequent acylation.

The invention also includes formulations containing effective amounts of such compounds, and methods for administering same to patients for the control and prophylaxis of cardiovascular disorders.

16 Claims, No Drawings

SUBSTITUTED 3-AMINOSYNDONE IMINES, A PROCESS FOR THEIR PREPARATION AND THEIR USE

This is a continuation-in-part of copending application Ser. No. 07/349,236 filed on May 9, 1989 now abandoned.

The invention relates to pharmacologically active substituted 3-aminosydnone imines of the general formula I

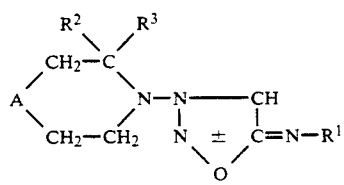

and their pharmacologically acceptable acid addition salts, in which

A denotes the radical $-CH_2-$, $-O-$, $-S(O)_n-$, $-N(R^4)-$ or a direct bond;

$R^1$ denotes hydrogen or the radical $-COR^5$;

$R^2$, $R^3$ denote alkyl having 1 to 4 C atoms;

$R^4$ denotes alkyl having 1 to 4 C atoms; hydroxyalkyl having 2 to 4 C atoms; phenylalkyl having 1 to 4 C atoms in the alkyl radical;

$R^5$ denotes an aliphatic radical having 1 to 4 C atoms which may also be substituted by alkoxy having 1 to 3 C atoms; a cycloaliphatic radical having 5 to 7 C atoms; a bicycloaliphatic radical having 7 to 14 C atoms; a tricycloaliphatic radical having 7 to 16 C atoms; an alkoxy radical having 1 to 6 C atoms; an aryloxy radical having 6 to 10 C atoms; an alkoxycarbonyl radical having a total of 2 to 7 C atoms; an aryl radical having 6 to 10 C atoms; an aryl radical having 6 to 10 C atoms which is mono-, di- or trisubstituted by 1 to 3 halogen atoms and/or 1 to 3 alkyl radicals having 1 to 3 C atoms and/or 1 to 3 alkoxy radicals having 1 to 3 C atoms and/or 1 or 2 nitro groups;

n denotes the number 0, 1 or 2.

The invention in addition relates to a process for the preparation of the compounds according to the invention and to their use.

If A denotes one of the radicals $-CH_2-$, $-O-$, $-S(O)_n-$ or $-N(R^4)-$, the radical of a heterocyclic 6-membered ring having one heteroatom (N) or having two hetero atoms (N,O or N,S or N,N), which is dialkylated in the manner indicated, is in the 3-position of the sydnone imine. If A denotes a direct bond, a pyrrolidine radical dialkylated in the 2,2-position is in the 3-position of the sydnone imine.

Of the divalent radicals standing for A, the radicals: $-CH_2-$, $-O-$ and $-N(R^4)-$ are preferred.

Aliphatic radicals, alkyl radicals, hydroxyalkyl radicals and alkoxy radicals may be straight-chain or branched. This also applies if they occur as substituents of other radicals, for example as substituents of aryl radicals, or combined with other radicals, for example as phenalkyl or as alkoxycarbonyl.

The alkyl radicals standing for $R^2$ and $R^3$ may be identical or different. They are usually identical. Suitable radicals for $R^2$ and $R^3$ are primarily straight-chain alkyl radicals. The radicals $R^2$ and $R^3$ particularly preferably denote methyl.

For $R^4$, alkyl having 1 to 4 C atoms, in particular methyl, ethyl, isopropyl, tert.-butyl and benzyl, is preferred.

As aliphatic radicals standing for $R^5$, alkyl radicals having 1 to 4 C atoms are particularly suitable. As aliphatic radicals standing for $R^5$, which are substituted by alkoxy having 1 to 3 C atoms, the methoxymethyl radical may be mentioned in particular. As cycloaliphatic radicals standing for $R^5$, cycloalkyl radicals having 5 to 7 C atoms, in particular cyclopentyl, and preferably cyclohexyl, are primarily suitable. As a bicycloaliphatic radical standing for $R^5$, the 2,6,6-trimethylbicyclo(3.1.1-)heptan-3-yl (=3-pinanyl) is particularly suitable. As a tricycloaliphatic radical standing for $R^5$, the tricyclo(3.3.1.1$^{3,7}$)decan-1-yl (=adamantanyl) is particularly suitable. As alkoxy radicals standing for $R^5$, those having 1 to 4 C. atoms, primarily methoxy and ethoxy radicals, are particularly suitable. As alkoxycarbonyl radicals standing for $R^5$, those having a total of 2 to 4 C atoms, primarily the ethoxycarbonyl radical, are particularly suitable. As aryl radicals standing for $R^5$, $\alpha$- or $\beta$-naphthyl radicals, for example, but in particular the phenyl radical, may be mentioned. As aryloxy radicals standing for $R^5$, $\alpha$- or $\beta$-naphthoxy radicals, for example, but in particular the phenoxy radical, may be mentioned. The aryl radicals standing for $R^5$ may be mono-, di- or trisubstituted, where, however, even on trisubstitution, only a maximum of 2 nitro groups may be present, such as, for example, 2-methyl-4,6-dinitrophenyl and 2-chloro-6-methyl-4-nitrophenyl. As halogen substituents for the aryl radicals, for example, chlorine and bromine atoms are suitable. Substituted aryl radicals standing for $R^5$ which may be mentioned in particular are: methylphenyl (=tolyl), nitrophenyl and chlorophenyl, in particular 4-nitrophenyl and 4-chlorophenyl.

The following are preferred for $R^5$: alkyl radicals having 1 to 4 C atoms, alkoxy radicals having 1 or 2 C atoms, cycloalkyl radicals having 5 to 7 C atoms and phenyl. The following are very particularly preferred: methyl, ethyl, isopropyl, tert.-butyl, methoxy, ethoxy, isopropoxy, cyclohexyl, phenyl, 4-chlorophenyl.

The following are preferred for $R^1$: hydrogen and $-COR^5$, where $R^5$ has the meanings previously indicated as preferred and, in particular, the meanings previously indicated as particularly preferred.

A compound of the general formula I can be prepared by a process in which a compound of the general formula II

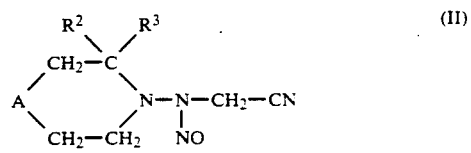

in which A, $R^2$ and $R^3$ have the meanings already mentioned, is cyclized to give a compound of the general formula Ia

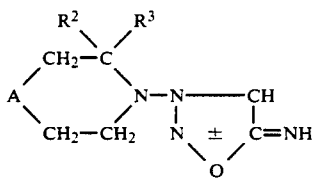

(Ia)

and in which this compound or an acid addition salt thereof is acylated, in the case in which it is intended to prepare a compound of the formula I having $R^1=$—$COR^5$, with an acylating agent which introduces the radical —$COR^5$, and the compound thus obtained is optionally converted into a pharmacologically acceptable acid addition salt.

The cyclization of the compounds II to give the compounds Ia is carried out in a suitable organic or inorganic solvent, dispersant or diluent with the addition of a cyclizing agent, normally at temperatures from —10° C. to 40° C., in particular 0 to 40° C., preferably at 0° to 20° C.

Suitable cyclizing agents are those which establish a pH below 3 in aqueous solution, i.e., for example, mineral acids, such as sulphuric, nitric or phosphoric acid, preferably hydrogen chloride, but also strong organic acids, such as trifluoroacetic acid. The cyclization is normally carried out with ice cooling.

0.1 to 10 mol, preferably 1 to 5 mol, of the cyclizing agent are used, for example, relative to 1 mol of the compound of the formula II. The cyclizing agent is normally employed in excess. The use of hydrogen chloride as the cyclizing agent, which is normally introduced into the reaction mixture to saturation, is particularly convenient. The corresponding acid addition salts of the compound Ia is normally obtained in the cyclization.

Suitable solvents, dispersants or diluents are, for example: alcohols, for example those having 1 to 8 C atoms, in particular those having 1 to 6 C atoms, preferably those having 1 to 4 C atoms, such as, for example, methanol, ethanol, i- and n-propanol, i-, sec- and tert-butanol, n-, i-, sec-, tert-pentanol, n-hexanol, 2-ethylbutanol, 2-ethylhexanol, isooctyl alcohol, cyclopentanol, cyclohexanol, methylcyclohexanol (mixture), benzyl alcohol; ethers, in particular those having 2 to 8 C. atoms in the molecule such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane, bis-β-methoxyethyl ether; oligoethylene glycol dimethyl ethers such as, for example, tetraglyme or pentaglyme; carboxylic acid alkyl esters, in particular those having 2 to 10 C atoms in the molecule such as, for example, methyl, ethyl, butyl or isobutyl formate, methyl, ethyl, propyl, isopropyl, butyl, isobutyl or sec-butyl, amyl, isoamyl, hexyl, cyclohexyl or benzyl acetate, methyl, ethyl or butyl propionate; ketones, in particular those having 3 to 10 C atoms in the molecule such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone, acetophenone; aliphatic hydrocarbons such as, for example, hexane, heptane, low- and high-boiling petroleum ethers, petroleum spirits and white spirit; cycloaliphatic hydrocarbons such as, for example, cyclopentane, cyclohexane, methylcyclohexane, tetralin, decalin; aromatic hydrocarbons such as, for example, benzene, toluene, o-, m- and p-xylene, ethylbenzene; halogenated aliphatic or aromatic hydrocarbons such as, for example, methylene chloride, chloroform, carbon tetrachloride, 1,2-dichloroethane, chlorobenzene, dichlorobenzene; hexamethylphosphoramide; sulphoxides such as, for example, dimethyl sulphoxide; tetramethylsulphone; water. Mixtures of different solvents or dispersants can also be used, for example water-methanol or preferably ethyl acetate-methanol.

The compounds of the formula Ia are compounds of the general formula I according to the invention in the case in which $R^1$ is hydrogen.

The acylation of the compound of the formula Ia, which may also be present in the form of an acid addition salt, in order to introduce the radical $R^1=$—$COR^5$ can be carried out in a manner known per se using a suitable acylating agent of the formula III

(III)

in which X represents a radical which can be removed by a nucleophile.

In formula III, X denotes, for example, in particular halogen, preferably —Cl or —Br; —OH; —O—alkyl, in particular having 1 to 5 C atoms; —O—aryl, in particular where the aryl radical is a phenyl radical which may also be monosubstituted or polysubstituted by alkyl, in particular methyl, and/or nitro and, for example is a tolyl, dinitrophenyl or nitrophenyl radical; —O—CO—$R^5$; —O—CO—O—alkyl, in particular having 1 to 5 C atoms in the alkyl radical, or the radical of an azole or benzazole bonded via an N atom and having at least 2N atoms in the quasi-aromatic five-membered ring.

The acrylation is expediently carried out in liquid phase in the presence of an inert solvent, dispersant or diluent or in an excess of the acylating agent, expediently with stirring.

In the acylation, the molar ratio between the compound of the formula Ia and the acrylating agent of the formula III is 1:1. The acylating agent of the formula III is expediently employed in a slight molar excess. Excesses of up to 30 mol % are usually sufficient, i.e. the molar ratio between the compound of the formula Ia and the acylating agent of the formula III is normally 1: (1 to 1.3), preferably 1: (1 to 1.2). If an acid is eliminated in the acylation reaction, the addition of an acid entrainer such as, for example, an alkali metal hydroxide such as, for example, sodium hydroxide, potassium hydroxide or lithium hydroxide, a tertiary organic amine such as, for example, pyridine or triethylamine, an alkali metal carbonate or alkali metal bicarbonate such as, for example, sodium carbonate or sodium bicarbonate, or an alkali metal salt of a weak organic acid such as, for example, sodium acetate is expedient. Suitable catalysts such as, for example, 4-dimethylaminopyridine can also be added to the acylation reaction.

The acylation can in principle be carried out at temperatures between —10° C. and the boiling point of the solvent, dispersant or diluent used. In many cases, the reaction is carried out at 0° to 50° C., in particular at 0° to 30° C. and preferably at room temperature.

The compounds of the formula III are acylating agents and thus represent, for example: for X=halogen, acid halides or haloformic acid esters, of which acid chlorides and chloroformic acid esters are preferred; for —OH, carboxylic acids; for —O—alkyl and —O—aryl esters, of which the tolyl, 2,4-dinitro or 4-nitrophenyl esters are preferred; for —O—CO—R$^5$, anhydrides; for —O—CO—O—alkyl, mixed carboxylic acid carbonic acid anhydrides; or heterocyclic amides or azolides, in particular of N,N'-carbonyldiazoles such as, for example, N,N'-carbonyldiimidazole, 2,2'-carbonyl-1,2,3-ditriazole, 1,1'-carbonyl-1,2,4-ditriazole, N,N'-carbonyl-dipyrazole, 2,2'-carbonyl-ditriazole (compare, for example, H. A. Staab, M. Lücking and F. H. Dürr, Chem. Ber. 95, (1962), 1275 ff, H. A. Staab and A. Mannschreck, Chem. Ber. 95, (1962), 1284 ff.; H. A. Staab and W. Rohr, "Sunthesen mit heterocyclischen Amiden (A zoliden)" ("Syntheses with heterocyclic amides (azolides)") in "Neuere Methoden der Prärativen Organischen Chemie" ("Newer Methods of Preparative Organic Chemistry"), Volume V, Verlag Chemie, 1967, p. 53 ff., in particular p. 65 to 69). The acrylating agents of the formula III can be prepared by processes known per se.

In the use of a carboxylic acid as an acylating agent, the addition of activating agent which has the object of increasing or activating the acylating potential of the carboxylic acid or converting the carboxylic acid in situ or preferably shortly before the reaction with the compound of the formula Ia into a reactive carboxylic acid derivative of the formula III is expedient. Suitable activating agents of this type are, for example: N,N'-disubstituted carbodiimides, in particular if they contain at least one secondary or tertiary alkyl radical such as, for example, diisopropyl-, dicyclohexyl- or N-methyl-N'-tert.-butyl-carbodiimide (compare Methodicum Chimicum, Verlag G. Thieme, Stuttgart, Vol. 6, (1974), p. 682/683, and Houben-Weyl, Methoden der Org. Chemie (Methods of Org. Chemistry), Vol. 8, (1952), p. 521/522); carbonic acid derivatives such as, for example, phosgene, chloroformic acid esters, in particular having 1 to 5 C atoms in the alkyl radical (compare, for example Tetrahedron Letters 24 (1983), 3365 to 3368); carboxylic acid esters such as, for example, N,N'-disuccinimido carbonate, diphthalimido carbonate, 1,1'-(carbonyldioxy)-dibenzo-triazole, or di-2-pyridyl carbonate (compare, for example, Tetrahedron Letters, Vol. 25, No. 43, 4943–4946), optionally in the presence of suitable catalysts such as, for example, 4-dimethylaminopyridine. In addition, suitable activating agents are N,N'-carbonyldiazoles such as, for example, N,N'-carbonyldiimidazole, 2,2'-carbonyl-1,2,3-ditriazole, 1,1'-carbonyl-1,2,4-ditriazole, N,N'-carbonyl-dipyrazole, 2,2'-carbonyl-ditetrazole, N,N'-carbonyl-benzimidazole or N,N'-carbonylbenzotriazole (compare, for example, H. A. Staab, M. Lücking and F. H. Dürr, loc. cit.; H. A. Staab and A. Mannschreck loc. cit.; H. A. Staab and W. Rohr loc. cit.). Commercial N,N'-carbonyl-diimidazole is frequently used as N,N'-carbonyl-diazole. However, the other N,N'-carbonylazoles are also easily accessible from the respective azole and phosgene.

Suitable activating agents for carboxylic acids are additionally: derivatives of oxalic acid, such as, for example, oxalyl chloride (compare, for example, GB Patent Specification 2,139,225) or N,N'-oxalyl-diazoles such as, for example, 1,1'-oxalyldi-imidazole, 1,1'-oxalyldi-1,2,4-triazole and 1,1'-oxalyldi-1,2,3,4-tetrazole (compare, for example, Shizuaka Murata, Bull. Chem. Soc. Jap. 57, 3597-3598 (1984)); methyl ethyl phosphinic anhydride (compare, for example, German Offenlegungsschrift 3,101,427; cf. U.S. Pat. No. 4,426,325); diphosphorus tetraiodide (Chem. Lett. 1983, 449); dialkyl disulphite (Indian J. Chem. 21, 259 (1982)); or other reactive agents.

Suitable solvents, dispersants or diluents are, for example, those which have been mentioned for carrying out the cyclization, and moreover also, for example, pyridine and amides such as, for example, dimethylformamide. In addition to water, polar organic solvents, such as dimethylformamide, dimethyl sulphoxide or pyridine are preferred for the acylation. Solvent mixtures such as, for example, a mixture of water and methylene chloride are also suitable.

The substituted 3-amino-sydnone imines of the general formula I form acid addition salts with inorganic or organic acids. Inorganic or organic acids are suitable for the formation of acid addition salts of this type. Suitable acids are, for example, hydrogen chloride, hydrogen bromide, naphthalenedisulphonic acids, in particular naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts can be prepared as is customary by combining the components, expediently in a suitable solvent or diluent.

In the synthesis of the compounds of the formula Ia, the acid addition salts are normally obtained. If desired, the free compounds of the general formula I or Ia can be obtained from the acid addition salts in a known manner, i.e. by dissolving or suspending in water and rendering alkaline, for example with sodium hydroxide solution, and then isolating.

The required starting compounds of the general formula II can be prepared in a manner known per se by Strecker's aminonitrile synthesis from compounds of the general formula IV

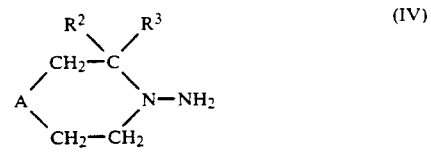

in which A, R$^2$ and R$^3$ have the meanings already mentioned, by reaction with formaldehyde and hydrocyanic acid or sodium cyanide in a suitable solvent, for example water, a compound of the general formula V

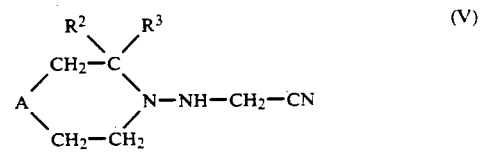

first being formed, which is converted by nitrosylation into the compound II. The nitrosylation is carried out in a known manner in a suitable solvent, preferably in water, for example at temperatures from 0° to 10° C. The nitrous acid is in this case normally produced from an alkali metal nitrite, for example sodium nitrite, and hydrochloric acid. It is expedient to adjust the aqueous solution of the compound V to a pH of 1 to 3 using hydrochloric acid and to add the alkali metal nitrite dropwise in the form of an aqueous solution to the stirred and cooled solution of the compound.

The solution of the compound II thus obtained can be subjected directly to the cyclization reaction. However, normally it is fitting to first take up the nitroso compound II in a suitable organic solvent and to carry out the cyclization to the compound of the formula Ia in it, if appropriate after addition of a further solvent.

Some of the compounds of the general formula IV are known or can be prepared, starting from compounds of the general formula VI

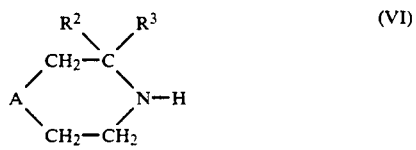

by a process in which either a) a compound of the formula VI is nitrosylated to give the N-nitroso compound VII and subsequently reduced, expediently with lithium aluminium hydride:

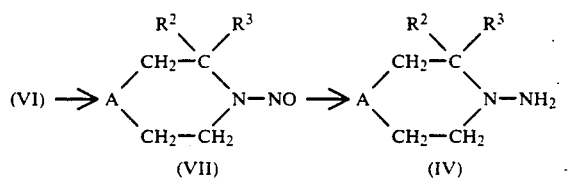

or in which in a manner known per se b) a compound of the formula VI is converted using potassium cyanate in acidic medium into the urea derivative VIII which is then converted by the Hoffmann degradation into the compound IV by oxidation with sodium hypochlorite.

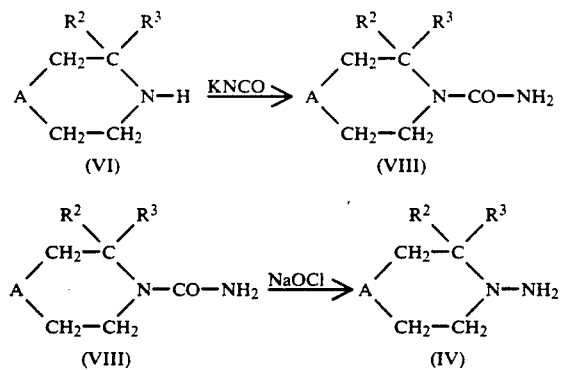

The preparation of the starting compounds of the formulae IV and VI is known. Starting compounds of the formula VI can be prepared, for example, from compounds of the general formulae IX or X

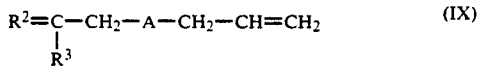

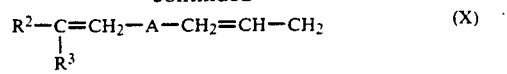

in which $R^2$ and $R^3$ and A have the meanings already indicated and which can be prepared by methods which are known per se, by ring closure with ammonia. The reaction with ammonia may be carried out at temperatures from 20° to 150° C., preferably at 60° to 100° C., with or without solvent.

The compound 3,3-dimethyl-1,4-thiazine 1,1-dioxide can be prepared from methallylsulphonylethanol and hydrazine hydrate. This reaction can also be applied to other starting compounds of the formula IV.

The preparation of the starting compound IV is described, for example, in DE-A-2,351,865 (cf. U.S. Pat. Nos. 3,943,098 and 4,061,631). Other starting compounds of the formulae IV and VI can be prepared analogously to the previously mentioned instructions.

The compounds of the general formula I and their pharmacologically acceptable acid addition salts have useful pharmacological properties. Their effect on the cardiovascular system is particularly pronounced. Compared with known sydnone imine compounds substituted in the 3-position, for example those of EP-B-59,356 (cf. U.S. Pat. Nos. 4,436,743 and 4,551,454), and also the commercially available structurally similar compound molsidomin, they surprisingly possess a substantially longer duration of action. For example, they lower the blood pressure as well as the pulmonal artery pressure and the left ventricular end-diastolic pressure and thus contribute to relieve the action of the heart in the sense of an antianginal action, without provoking reflex tachycardia at the same time.

Due to inhibition of thrombocyte aggregation, the compounds may additionally show antithrombotic effects.

The compounds of the formula I and their pharmacologically acceptable acid addition salts may therefore be administered to humans as medicaments alone, in mixtures with one another or in the form of pharmaceutical preparations which allow enteral or parenteral use and which contain an effective dose of at least one compound of the formula I or an acid addition salt thereof as active constituent, in addition to customary pharmaceutically acceptable excipients and additives.

The medicaments may be administered orally, for example in the form of pills, tablets, lacquered tablets, coated tablets, hard and soft gelatin capsules, solutions, syrups, emulsions or suspensions or aerosol mixtures. However, administration may also take place rectally, for example in the form of suppositories, or parenterally, for example in the form of injection solutions, or percutaneously, for example in the form of ointments or tinctures.

In order to prepare the pharmaceutical preparations, pharmaceutically inert inorganic or organic excipients may be used. For the preparation of pills, tablets, coated tablets and hard gelatin capsules, for example lactose, maize starch or derivatives thereof, talc, stearic acid or salts thereof etc. may be used. Excipients for soft gelatin capsules and suppositories are, for example, fats, waxes, semisolid and liquid polyols, natural or hardened oils etc. Suitable excipients for the preparation of solutions and syrups are, for example, water, sucrose, dextrose, glucose, polyols etc. Suitable excipients for the preparation of injection solutions are, for example, water, alcohols, glycerol, polyols or vegetable oils.

In addition to the active compounds and excipients, the pharmaceutical preparations may further contain additives such as, for example, fillers, extenders, disintegrants, binders, lubricants, wetting agents, stabilizers, emulsifiers, preservatives, sweeteners, colorants, flavourings or aromatizers, buffer substances, and in addition solvents or solubilizers or agents for achieving a depot effect, and also salts for changing the osmotic pressure, coating agents or antioxidants. They may also contain two or more compounds of the formula I or their pharmacologically acceptable acid addition salts and other therapeutically active substances.

Other therapeutically active substances of this type are, for example: β-receptor blockers such as, for example, propranolol, pindolol, metoprolol; vasodilators such as, for example, carbochromen; sedatives such as, for example, barbituric acid derivatives, 1,4-benzodiazepines and meprobamate; diuretics such as, for example, chlorothiazide; agents which increase cardiac tone such as, for example digitalis preparations; hypotensive agents such as, for example, hydralazine, dihydralazine, prazosine, clonidine, rauwolfia alkaloids; agents which lower the fatty acid level in the blood such as, for example, benzafibrate, fenofibrate; and agents for thrombosis prophylaxis such as, for example, phenprocoumon.

The compounds of the formula I, their pharmacologically acceptable acid addition salts and pharmaceutical preparations which contain the compounds of the formula I or their pharmacologically acceptable acid addition salts as active compounds may be used in humans in the control or prophylaxis of disorders of the cardiovascular system, for example as antihypertensive medicaments in the various forms of high blood pressure, and in the control or prophylaxis of angina pectoris etc. The dosage may vary within wide limits and is to be adjusted to the individual conditions in each individual case. In general, a daily dose of about 0.5 to 100 mg, preferably 1 to 20 mg, per human individual is suitable on oral administration. Even with other administration forms the daily dose, on account of the good absorption of the active compound, lies in similar dose ranges, i.e. in general also at 0.5 to 100 mg/human. The daily dose is normally divided into a number of, for example 2 to 4, part administrations.

The pharmacological action of the compounds of the formula I was determined by a modified method of Godfraind and Kaba (Arch. Int. Pharmacodyn. Ther. 196, (Suppl.) 35 to 49, 1972) and of Schümann et al (Naunyn-Schmiedeberg's Arch. Pharmacol. 289, 409 to 418, 1975). In this connection, spiral strips of the pulmonal artery of the guinea pig are depolarized using 40 mmol/l of potassium after equilibration in calcium-free Tyrode solution. An addition of 0.5 mmol/l of $CaCl_2$ then induces a contraction. The relaxant effect of the test substance is determined by cumulative addition in ½ log 10 graduated concentrations. The concentration of the test substance which inhibits the concentration by 50% ($=IC_{50}$, mol/l) is determined from the concentration-effect curve (abscissa: $-\log$ mol/l of test substance, ordinate: % inhibition of the maximum concentration, average value of 4 to 6 vessel strips). The $IC_{50}$ values thus obtained are indicated in the following table. As the comparision with the $IC_{50}$ value $3.10^{-4}$ for the known compound molsidomin (N-ethoxycarbonyl-3-morholino-sydnone imine), compare DE-B-1,695,897, shows, the values for the compounds of the formula I are considerably more favourable.

| $IC_{50}$ values in mol/l: duration of action in min: | | |
|---|---|---|
| | $IC_{50}$ | Duration of action |
| a) 3-(3,3-Dimethylmorpholin-4-yl)-sydnone imine hydrochloride | $1 \cdot 10^{-6}$ | 120 |
| b) 3-(2,2-Dimethylpiperidin-1-yl)-sydnone imine hydrochloride | $1 \cdot 10^{-6}$ | 130 |
| c) 3-(4-Isopropyl-2,2-dimethyl-piperazin-1-yl)-sydnone imine dihydrochloride | $1 \cdot 10^{-6}$ | 120 |
| d) 3-(3,3-Dimethyl-1,4-tetrahydrothiazin-1,1-dioxid-4-yl)-sydnone imine hydrochloride | $6 \cdot 10^{-6}$ | 240 |
| e) 3-(3,3-Dimethyl-tetrahydro-1,4-thiazin-4-yl)-sydnone imine hydrochloride | $2 \cdot 10^{-6}$ | 200 |
| f) N-p-Anisoyl-3-(4-isopropyl-2,2-dimethyl-piperazin-1-yl)-sydnone imine dihydrochloride | $2 \cdot 10^{-5}$ | 130 |
| g) 3-(3,3-Dimethyl-perhydro-1-oxo-1,4-thiazin-4-yl)-sydnone imine hydrochloride | $3 \cdot 10^{-6}$ | 270 |
| h) N-Ethoxycarbonyl-3-morpholino-sydnone imine | $3 \cdot 10^{-4}$ | 80 | a to g: Compounds according to the invention
h: Comparison compound molsidomin

EXAMPLE 1

3-(3,3-Dimethylmorpholin-4-yl)-sydnone imine hydrochloride a) 4-Nitroso-3,3-dimethylmorpholine A solution of 17 g of sodium nitrite is added dropwise at 0° to a mixture of 23 g of 3,3-dimethylmorpholine and 20 g of conc. hydrochloric acid in 30 ml of water and the reaction mixture is stirred for 15 hours. The product is extracted by shaking with diethyl ether. After drying over sodium sulphate and concentrating, a yellow oil remains. Yield: 21.9 g, The 3,3-dimethylmorpholine required as starting material can be prepared according to J. Org. Chem. 11, 288 (46).

b) 4-Amino-3,3-dimethylmorpholine 21.6 g of the nitroso compound obtained in step a are dissolved in 150 ml of tetrahydrofuran and 6.3 g of lithium alanate are added in portions. An exothermic reaction occurs after addition of ⅓ of the reducing agent. The temperature is kept under 50° C. and the mixture is subsequently stirred at room temperature for 15 hours after completion of the addition. The flask is then cooled with ice and ice water is cautiously added dropwise for just as long as hydrogen is still evolved. Precipitated aluminium hydroxide is filtered off with suction and the filtrate is extracted three times by shaking with diethyl ether. The aluminium hydroxide is suspended using diethyl ether and filtered off with suction, and the organic phases are combined, washed with saturated sodium chloride solution, then dried over sodium sulphate and distilled. A colourless oil is thus obtained. Yield: 14.6 g.

c) N-Nitroso-N-3,3-dimethyl-morpholin-4-yl-amino-acetonitrile 14.4 g of the 4-amino-3,3-dimethylmorpholine obtained in step b are dissolved in 70 ml of water, 11 g of conc. hydrochloric acid are added and the mixture is cooled to 0°–5° C. A solution of 8.6 g of potassium cyanide in 25 ml of water and then 11 g of 39% strength aqueous formalin solution are then added dropwise with stirring. This mixture is subsequently stirred for 4 hours, cooled to 5° C. and adjusted to pH=1 by addition of conc. hydrochloric acid, and a solution of 7.6 g of sodium nitrite in 20 ml of water is added dropwise. The reaction is complete after 1 hour. The product is extracted by shaking with ethyl acetate, and the ethyl acetate solution is dried and concentrated. A red-brown oil remains. Yield: 15 g.

d) 3-(3,3-Dimethyl-morpholin-4-yl)-sydnone imine hydrochloride

The nitroso compound from step c is dissolved in 70 ml of ethanol, and hydrogen chloride is introduced into this solution with ice cooling until it is saturated. After 1 day, the precipitate is filtered off with suction and the filtrate is concentrated. The remaining oil is stirred with ethyl acetate, and the solid is filtered off with suction and recrystallized from isopropanol. Yield: 5.2 g; m.p.: 155° C. (Decomposition).

The following sydnone imines can be prepared in an analogous manner:

EXAMPLE 2

3-(2,2-Dimethylpiperidin-1-yl)-sydnone imine hydrochloride

Yield: 45% of theory; m.p.: 168° C. (Decomposition).

The preparation of the 2,2-dimethylpiperidine required as starting material is described in J. Org. Chem. 27, 1290 (1962).

EXAMPLE 3

3-(2,2-Dimethyl-pyrrolidin-1-yl)-sydnone imine hydrochloride

Yield: 41% of theory; m.p.: 177° C. (Decomposition).

The preparation of the 2,2-dimethylpyrrolidine required as starting material is described in Org. Synthesis Coll. Vol. IV, 354.

EXAMPLE 4

3-(4-Isopropyl-2,2-dimethyl-piperazin-1-yl)-sydnone imine dihydrochloride

Yield: 38% of theory; m.p.: 152° C. (Decomposition).

EXAMPLE 5

N-(4-Chlorobenzoyl)-3-(2,2-dimethylpiperidin-1-yl)-sydnone imine

A solution of 1.6 g of 4-chlorobenzoyl chloride in 20 ml of methylene chloride is added at 0° C. to a solution of 2.1 g of 3-(2,2-dimethylpiperidin-1-yl)-sydnone imine hydrochloride and 1.5 g of sodium bicarbonate in 15 ml of water. The mixture is stirred at room temperature for 15 hours, and the methylene chloride phase is separated off, dried and concentrated. The residue is recrystallized from diisopropyl ether. Yield: 1.4 g; m.p.: 138°–141° C.

EXAMPLE 6

N-Acetyl-3-(2,2-dimethylpiperidin-1-yl)-sydnone imine

The preparation is carried out analogously to Example 5, acetic anhydride being used instead of 4-chlorobenzoyl chloride. Yield: 73% of theory; m.p.: 83°–84° C.

EXAMPLE 7

N-Ethoxycarbonyl-3-(2,2-dimethylpiperidin-1-yl)-sydnone imine

The preparation is carried out analogously to Example 5, ethyl chloroformate being used instead of 4-chlorobenzoyl chloride. Yield: 65% of theory; m.p.: 70°–75° C.

EXAMPLE 8

N-Cyclohexylcarbonyl-3-(3,3-dimethylmorpholin-4-yl)-sydnone imine

The preparation is carried out analogously to Example 5, cyclohexanecarbonyl chloride and 3-(3,3-dimethylmorpholin-4-yl)sydnone imine hydrochloride being employed. Yield: 68% of theory; m.p.: 91°–93° C.

EXAMPLE 9

N-Isobutyroyl-3-(2,2-dimethyl-4-isopropyl-piperazin-1-yl)-sydnone imine

The preparation is carried out analogously to Example 5, isobutyryl chloride and 3-(2,2-dimethyl-4-isopropylpiperazin-1-yl)-sydnone imine dihydrochloride being employed. Yield: 61% of theory; m.p.: 71°–73° C.

EXAMPLE 10

3-(3,3-Dimethyl-1,4-tetrahydrothiazine-1,1-dioxide-4-yl)sydnone imine hydrochloride a)

4-Amino-3,3-dimethyl-1,4-tetrahydrothiazine-1,1-dioxide hydrogensulphate

A mixture of 57 g of 2,2-dimethyl-1,4-oxathiane-4,4-dioxide of the formula XI

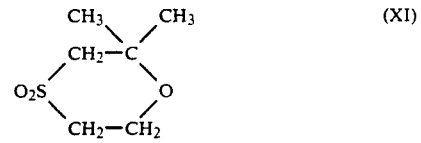

45.5 g of hydrazine hydrate and 650 ml of water is heated in an autoclave at 180° C. for 6 h. After cooling, the mixture is concentrated on a rotary evaporator, the residue is dissolved in as little water as possible, and the solution is rendered acidic with 50% strength sulphuric acid and stirred at 0° C. The precipitate is filtered off with suction, washed with ethanol and dried. Yield: 25 g; M.p. 206° C. (dec.).

b)

4-Cyanomethylamino-3,3-dimethyl-1,4-tetrahydrothiazine-1,1-dioxide

A solution of 26 g of 4-amino-3,3-dimethyl-1,4-tetrahydrothiazine-1,1-dioxide hydrogensulphate (step a) in 300 ml of water is cooled to 5° C. and 7.8 g of potassium cyanide are added. A pH of 7 to 7.5 is established by addition of sodium carbonate solution and 7.7 g of a 39% strength formalin solution is added. The mixture is then stirred at room temperature for 6 h, the pH being kept at 7 by addition of some hydrochloric acid or sodium carbonate solution. The product is separated off by shaking twice with ethyl acetate and after drying and concentrating the solvent remains behind as an oil which solidifies after a short time. Yield: 15 g; M.p. 84° to 85° C.

c)
3-(3,3-Dimethyl-1,4-tetrahydrothiazine-1,1-dioxide-4-yl)sydnone imine hydrochloride 6.8 g of sodium nitrite are added with cooling and under nitrogen to a mixture consisting of 14 g of 4-cyanomethylamino-3,3-dimethyl-1,4-tetrahydrothiazine-1,1-dioxide (step b), 200 ml of ice-water, 10 ml of 10N hydrochloric acid and 200 ml of ethyl acetate and the mixture is further stirred at room temperature for 1 h. The organic phase is separated off, dried and 30 ml of 25% strength isopropanolic hydrochloric acid are added at 0° C. After 15 h, the mixture is concentrated in a water jet vacuum and the residue is boiled with 500 ml of ethyl acetate. After cooling, the solid is filtered off with suction and dried. Yield: 5.5 g; M.p. 220° C. dec.

| Analysis: $C_8H_{15}ClN_4O_3S$ | | | |
| --- | --- | --- | --- |
| C | H | N | O |
| Calc. 34.0 | 5.3 | 19.8 | 17.0 |
| Found 33.7 | 5.4 | 20.0 | 16.7 |

The starting compound XI needed in step a can be prepared as follows (compare Arzneimittelforschung loc. cit.):

1 mol of KOH is dissolved in 1 mol of ethanol and 1 mol of 2-mercaptoethanol is added. 1 mol of 2,2-dimethyloxirane is added dropwise to this solution in the course of 60 min and with cooling. The mixture is then neutralized, the precipitate is filtered off, and the filtrate is concentrated and distilled in vacuo. 2-Hydroxy-2-methylpropyl 2-hydroxyethyl sulphide of boiling point 93° C. at 0.199 mbar is obtained.

0.5% by weight of phosphoric acid is added to the sulphide obtained and the sulphide is then oxidized by dropwise addition of 30% strength by weight $H_2O_2$ to give 2-hydroxy-2-methylpropyl 2-hydroxyethyl sulphone. This sulphone is obtained after concentration as a non-distillable oil.

A mixture of 32 g of 2-hydroxy-2-methylpropyl 2-hydroxyethyl sulphone and 5 g of $KHSO_4$ are heated to 120° C., after the cyclization is complete the mixture is cooled, the precipitate is filtered off, the filtrate is neutralized with potassium carbonate, the precipitate is again filtered off, and the filtrate is concentrated and distilled in vacuo at 0.532 mbar. The compound 2,2-dimethyl-1,4-oxathiane-4,4-dioxide has a boiling point of 100°–102° C. at this pressure. M.p.: 83° C.

EXAMPLE 11

N-Ethoxycarbonyl-3-(3,3-dimethyl-1,4-tetrahydrothiazine-1,1-dioxide-4-yl)sydnone imine 1.11 g of $NaHCO_3$ and a solution of 0.65 g of ethyl chloroformate in 20 ml of methylene chloride are added to a solution of 1.5 g of 3-(3,3-dimethyl-1,4-tetrahydrothiazine-1,1-dioxide-4-yl)sydnone imine hydrochloride (Example 1) in 20 ml of water cooled to 0° to 5° C. and the mixture is stirred at a temperature increasing to room temperature until evolution of gas is complete. The organic phase is separated off, dried and concentrated in a water jet vacuum, and the residue is recrystallized from ethyl acetate. Yield: 0.82 g M.p. 188°–190° C.

| Analysis: $C_{11}H_{18}N_4O_5S$ | | | |
| --- | --- | --- | --- |
| C | H | N | O |
| Calc. 41.5 | 5.7 | 17.6 | 25.2 |
| Found 41.5 | 5.6 | 17.8 | 24.9 |

EXAMPLE 12

N-p-Anisoyl-3-(3,3-dimethyl-1,4-tetrahydrothiazine-1,1-dioxide-4-yl)sydnone imine The compound is obtained analogously to Example 11 using p-anisoyl chloride instead of ethyl chloroformate. M.p.: 178° to 180° C.

| Analysis: $C_{16}H_{20}N_4O_5S$ | | | |
| --- | --- | --- | --- |
| C | H | N | O |
| Calc. 50.5 | 5.3 | 14.7 | 21.1 |
| Found 50.2 | 5.4 | 15.0 | 20.8 |

EXAMPLE 13

N-Cyclohexylcarbonyl-3-(3,3-dimethyl-1,4-tetrahydrothiazine-1,1-dioxide-4-yl)sydnone imine The compound is obtained analogously to Example 11 using cyclohexanecarbonyl chloride instead of ethyl chloroformate. M.p.: 150° to 151° C.

| Analysis: $C_{15}H_{24}N_4O_4S$ | | | |
| --- | --- | --- | --- |
| C | H | N | O |
| Calc. 50.6 | 6.7 | 15.7 | 18.0 |
| Found 50.5 | 6.5 | 15.8 | 18.0 |

EXAMPLE 14

3-(3,3-Dimethyltetrahydro-1,4-thiazin-4-yl)sydnone imine hydrochloride a) 2,2-Dimethylaziridine 100 g of 2-amino-2-methylpropan-1-ol are dissolved in 200 ml of water. A cold solution of 110 g of conc. sulphuric acid in 200 ml of water is then added dropwise with stirring and the water is then removed by distillation at normal pressure until an internal temperature of 115° C. is obtained. The mixture is then further distilled in a water jet vacuum up to a bath temperature of 180° C. and the contents of the flask are kept under these conditions until they are solid. The mixture is then heated further in a water jet vacuum and at 180° C. for 1 more hour.

A solution of 100 g of NaOH in 200 ml of water is added to the product, and it is comminuted and allowed to stand overnight. Water is removed from the suspension by distillation under normal pressure. 50 g of KOH are added with stirring to the residue and the mixture is stirred for 3 hours. After allowing to stand, the upper layer is separated off, 20 g of KOH are added and the mixture is allowed to stand overnight. The oil is poured off, 10 g of KOH are added and the mixture is distilled under normal pressure. Yield: 60.3 g.

b) 2-Hydroxyethyl 2-amino-2-methylpropyl sulphide 234 g of 2-mercaptoethanol are dissolved in 90 ml of dimethoxyethane. 63.3 g of 2,2-dimethylaziridine are added dropwise to this solution and the mixture is stirred at 70° C. for 4 hours and concentrated, and the residue is distilled in a water jet vacuum. B.p.: 141°-142° C. (at 20 mbar); M.p.: 49°-51°;

c) 3,3-Dimethyltetrahydro-1,4-thiazine

Hydrogen chloride is passed into a solution of 14.9 g of 2-hydroxyethyl 2-amino-2-methylpropyl sulphide (step b) in 100 ml of dimethoxyethane with stirring until it is saturated and 17.9 g of thionyl chloride are then added dropwise, and the mixture is stirred at room temperature for another hour and then heated at reflux for 1 hour. The solution is then concentrated in a water jet vacuum. The residue of 2-chloroethyl 2-amino-2-methylpropyl sulphide hydrochloride crystallizes out.

The hydrochloride obtained is dissolved in water, the solution is rendered strongly alkaline with potassium carbonate, the precipitate is taken up in 100 ml of toluene and the aqueous phase is again extracted by shaking with 2×30 ml of toluene. The organic phases are combined, dried over potassium carbonate and concentrated, and the residue is distilled in a water jet vacuum. Yield: 8.1 g B.p.: 73°-75° C. (at 20 mbar)

d) 4-Nitroso-3,3-dimethyltetrahydro-1,4-thiazine 12 ml of 10N HCl are added with cooling to a mixture of 15.7 g of 3,3-dimethyltetrahydro-1,4-thiazine (step c) and 60 ml of ice-water. A solution of 12.4 g of sodium nitrite in 40 ml of water is then added dropwise at 4° to 6° C. The mixture is subsequently stirred at room temperature for 4 hours, rendered alkaline with potassium carbonate and extracted by shaking with ethyl acetate. The organic phase is dried and concentrated in a water jet vacuum. Yield: 17.5 g; M.p.: yellow oil.

e) 4-Amino-3,3-dimethyltetrahydro-1,4-thiazine hydrochloride 4.4 g of lithium aluminium hydride are added in portions at 60°-65° C. to a solution of 17.2 g of 4-nitroso-3,3-dimethyl-tetrahydro-1,4-thiazine (step d) in 150 ml of tetrahydrofuran and the mixture is then heated to reflux for 2 hours. The suspension is cooled and a solution of 5 ml of water in 50 ml of tetrahydrofuran is added dropwise. After 20 minutes, 10 ml of 27% strength by weight sodium hydroxide solution are added dropwise and the mixture is allowed to stand for a few hours. The precipitate is then filtered off and the hydrochloride is precipitated in the ice-cooled filtrate. Yield: 12.2 g f) 4-(2-Cyanoethylamino)-3,3-dimethyltetrahydro-1,4-thiazine A solution of 6.1 g of KCN in 30 ml of water is added dropwise to a solution of 12.1 g of 4-amino-3,3-dimethyltetrahydro-1,4-thiazine hydrochloride (step e) cooled to −3° to −5° C. The pH of the solution is then adjusted to 7.2 with hydrochloric acid and 16.3 g of 39% strength by weight aqueous formaldehyde are then added, the pH being kept at 6 to 7. The mixture is subsequently stirred overnight at a temperature increasing to room temperature. The suspension is extracted by shaking with ethyl acetate, and the organic phase is dried and concentrated. Yield: 9.4 g; M.p.: oil.

g) 3-(3,3-Dimethyltetrahydro-1,4-thiazin-4-yl)sydnone imine hydrochloride 9.4 g of 4-(2-cyanoethylamino)-3,3-dimethyltetrahydro-1,4-thiazine (step f), 40 ml of ethyl acetate, 40 g of ice-water and 5 ml of 10N hydrochloric acid are cooled to −5° C. 5.3 g of sodium nitrite are introduced into this mixture and it is subsequently stirred at room temperature for 3 hours. The organic phase is separated off, dried and filtered off, and 20 ml of a saturated solution of HCl in isopropanol are added dropwise with cooling. The mixture is subsequently stirred overnight at room temperature. The precipitate is separated off and recrystallized from isopropanol. Yield: 5.9 g; M.p.: 172° C. (decomposition).

EXAMPLE 15

N-p-Anisoyl-3-(3,3-dimethyltetrahydro-1,4-thiazin-4-yl)sydnone imine 2 g of 3-(3,3-dimethyltetrahydro-1,4-thiazin-4-yl)sydnone imine hydrochloride (Example 14 g) are dissolved in 20 ml of ice-water and 1.7 g of $NaHCO_3$ are added. 1.7 g of p-anisoyl chloride, dissolved in 20 ml of ethyl acetate, are then added dropwise. After subsequently stirring overnight at room temperature, the phases are separated, the aqueous phase is extracted by shaking with ethyl acetate, and the organic phases are combined, dried and concentrated. The crystalline product obtained is recrystallized from isopropanol. Yield: 1,9 g; M.p.: 131° to 133° C.

EXAMPLE 16

N-Ethoxycarbonyl-3-(3,3-dimethyltetrahydro-1,4-thiazin-4-yl)sydnone imine

The compound is obtained analogously to Example 15 using ethyl chloroformate (1 g) instead of p-anisoyl chloride and is purified by stirring with petroleum ether. Yield: 1.8 g; M.p.: 110° to 112° C.

EXAMPLE 17

N-Methoxycarbonyl-3-(3,3-dimethyl-1,4-tetrahydrothiazine-1,1-dioxo-4-yl)sydnone imine The compound is obtained analogously to Example 11 using methyl chloroformate (0.6 g) instead of the ethyl ester and is recrystallized from ethyl acetate. Yield: 2.0 g; M.p.: 233° to 235° C. (dec.).

EXAMPLE 18

N-Butoxycarbonyl-3-(3,3-dimethyl-1,4-tetrahydrothiazine-1,1-dioxo-4-yl)sydnone imine hydrochloride The compound is obtained analogously to Example 11 using butyl chloroformate (0.8 g) instead of the ethyl ester and is precipitated from ethyl acetate as the hydrochloride using isopropanolic hydrochloric acid. Yield: 1.3 g; M.p.: 153° to 154° C. (dec.).

EXAMPLE 19

N-Butoxyacetyl-3-(3,3-dimethyl-1,4-tetrahydrothiazine-1,1-dioxo-4-yl)sydnone imine hydrochloride The compound is obtained analogously to Example 11 using 0.9 g of butoxyacetyl chloride instead of ethyl chloroformate and is precipitated from ethyl acetate as the hydrochloride using isopropanolic hydrochloric acid. Yield: 1.9 g; M.p.: 165° C. (dec.).

EXAMPLE 20

3-(3,3-Dimethyl-1,4-tetrahydrothiazine-1,1-dioxide-4-yl)sydnone imine hydrochloride 3 g of a 35% strength hydrogen peroxide solution are added at room temperature to a solution of 3 g of 3-(3,3- dimethyltetrahydro-1,4-thiazin-4-yl)sydnone imine (prepared according to Example 14) in 40 ml of glacial acetic acid. The temperature increases to 30° to 40° C. The mixture is stirred for 2 h and then concentrated in a water jet vacuum. The residue is stirred in isopropanol and recrystallized from methanol. Yield: 1.8 g; M.p.: 219° C. (dec.).

EXAMPLE 21

N-Ethoxycarbonyl-3-(3,3-dimethylmorpholin-4-yl)-sydnone imine hydrochloride

A solution of 3.0 g of 3-(3,3-dimethyl-morpholin-4-yl)-sydnone imine hydrochloride (Example 1d) in 25 ml of water is cooled to 0° to 5° C., 3.0 g of sodium carbonate and a solution of 1.5 g of ethyl chloroformate in 25 ml of methylene chloride are added and the mixture is stirred at 0° C. for 2 hours. The methylene chloride phase is separated off, dried over $Na_2SO_4$ and concentrated in a water jet vacuum. The remaining oil is stirred with diisopropyl ether. The precipitate formed is filtered off with suction and dried. Yield: 2.0 g; m.p.: 101° to 103° C.

The compounds of Examples 22 to 30 can be prepared analogously to Example 21:

EXAMPLE 22

N-Benzoyl-3-(3,3-dimethyl-morpholin-4-yl)-sydnone imine

The reaction is carried out analogously to Example 21, but benzoyl chloride is employed instead of ethyl chloroformate in step e). m.p.: 149°-151° C.

EXAMPLE 23

N-Pivaloyl-3-(3,3-dimethyl-morpholin-4-yl)-sydnone imine

The reaction is carried out as in Example 21, but pivaloyl chloride is employed instead of ethyl chloroformate in step e). m.p.: 111°-112° C.

EXAMPLE 24

N-p-Anisoyl-(3,3-dimethyl-morpholin-4-yl)-sydnone imine hydrochloride

The reaction is carried out analogously to Example 21, but p-anisoyl chloride is employed instead of ethyl chloroformate in step e). The compound obtained is dissolved in ethyl acetate and the hydrochloride is precipitated by passing in HCl. m.p.: 140° C. (decomposition).

EXAMPLE 25

N-Methoxyacetyl-(3,3-dimethyl-morpholin-4-yl)-sydnone imine

The reaction is carried out as in Example 21, but methoxyacetic anhydride is employed instead of ethyl chloroformate in step e). m.p.: 127°-130° C.

EXAMPLE 26

N-Acetyl-(3,3-dimethylmorpholin-4-yl)-sydnone imine

The reaction is carried out analogously to Example 21, but acetic anhydride is employed instead of ethyl chloroformate in step e). m.p.: 115° C.

EXAMPLE 27

N-o-Toluoyl-(3,3-dimethyl)-morpholin-4-yl)-sydnone imine

The reaction is carried out analogously to Example 21, but o-toluoyl chloride is employed instead of ethyl chloroformate in step e). m.p.: 154°-156° C.

EXAMPLE 28 n-Pivaloyl-3-(4-isopropyl-2,2-dimethyl-piperazin-1-yl)-sydnone imine a) 3-(4-Isopropyl-2,2-dimethyl-piperazin-1-yl)-sydnone imine dihydrochloride This compound is prepared analogously to Example 1a) to d), the equivalent amount of 4-isopropyl-2,2-dimethylpiperazine being employed instead of 3,3-dimethylmorpholine in step a). Yield: 38% of theory; m.p.: 152° C. (decomposition).

b) N-Pivaloyl-3-(4-isopropyl-2,2-dimethyl-piperazin-1-yl)-sydnone imine

A solution of 3.0 g of the compound from step a) in 30 ml of water is cooled to 0° C. and 2.8 g of sodium bicarbonate and a solution of 1.4 g of pivaloyl chloride in 20 ml of methylene chloride are added and the mixture is stirred at room temperature for 4 hours. The organic phase is separated off, dried and concentrated in vacuo. The partly oily residue is recrystallized from petroleum ether. Yield: 1.8 g; m.p.: 99° to 101° C.

EXAMPLE 29

N-p-Anisoyl-3-(4-isopropyl-2,2-dimethyl-piperazin-1-yl)-sydnone imine

The reaction is carried out analogously to Example 28 b), but p-anisoyl chloride is employed instead of pivaloyl chloride. m.p.: 137° C. (decomposition).

EXAMPLE 30

N-Ethoxycarbonyl-3-(4-isopropyl-2,2-dimethyl-piperazin-1-yl)-sydnone imine dihydrochloride The reaction is carried out analogously to Example 28 b), but ethyl chloroformate is employed instead of pivaloyl chloride. The oily residue obtained is converted into the dihydrochloride by treatment with ethyl acetate saturated with HCl gas. m.p.: 137° C. (decomposition).

EXAMPLE 31

3-(3,3-Dimethyl-perhydro-1-oxo-1,4-thiazin-4-yl)-sydnone imine-hydrochloride 1.2 g of a 35% strength aqueous hydrogen peroxide solution are added to a solution of 3 g of 3-(3,3-dimethyl-perhydro-1,4-thiazin-4-yl)-sydnone imine hydrochloride (step g of Example 14) at room temperature with stirring, whereupon the temperature rises somewhat. The mixture is stirred for 2 hours and then concentrated in a water jet vacuum and the residue is recrystallized from ethyl acetate. Yield: 2.5 g; m.p.: 192° C. (dec.).

EXAMPLE 32

N-p-Anisoyl-3-(3,3-dimethylperhydro-1-oxo-1,4-thiazin-4-yl)-sydnone imine 3 g of 3-(3,3-dimethyl-perhydro-1-oxo-1,4-thiazin-4-yl)-sydnone imine hydrochloride (Example 31) are dissolved in 20 ml of ice water and 2 g of NaHCO₃ are added. 2.1 g of p-anisoyl chloride, dissolved in 30 ml of ethyl acetate, are then added dropwise. The mixture is subsequently stirred for 3 hours, the temperature rising to room temperature. The phases are then separated, the aqueous phase is extracted by shaking with ethyl acetate, and the organic phases are combined, dried and concentrated. The crystalline product obtained is recrystallized from isopropanol. Yield: 1.8 g; m.p.: 183° to 185° C. (dec.).

EXAMPLE 33

N-Ethoxycarbonyl-3-(3,3-dimethyl-perhydro-1-oxo-1,4-thiazin-4-yl)-sydnone imine

The compound is obtained analogously to Example 32 using ethyl chloroformate (1.8 g) instead of p-anisoyl chloride and is recrystallized from isopropyl acetate. Yield: 1.4 g; m.p.: 138° C. (dec.).

EXAMPLE 34

N-Pivaloyl-3-(3,3-dimethyl-perhydro-1-oxo-1,4-thiazin-4-yl)-sydnone imine

The compound is obtained analogously to Example 32 using 2.1 g of pivaloyl chloride instead of p-anisoyl chloride and is recrystallized from diisopropyl ether. Yield: 1.3 g; m.p.: 110° C. (dec.).

EXAMPLE 35

N-Pivaloyl-3-(3,3-dimethyl-1,1-dioxo-tetrahydro-1,4-thiazin-4-yl)-sydnone imine

The compound is obtained analogously to Example 11 using pivaloylchloride (0.9 g) instead of the ethyl chloroformate and is recrystallized from isopropanole. Yield: 1.2 g; m.p.: 194°-6° C.

EXAMPLE 36

N-Isobutyroyl-3-(3,3-dimethyl-1,1-dioxo-tetrahydro-1,4-thiazin-4-yl)-sydnone imine The compound is obtained analogously to Example 11 using isobutyroylchloride (0.9 g) instead of ethyl chloroformate and is recrystallized from isopropanole. Yield: 1.3 g; m.p.: 132°-135° C.

EXAMPLE 37

N-Pivaloyl-3-(3,3-dimethyl-tetrahydro-1,4-thiazin-4-yl) sydnone imine

The compound is obtained analogously to Example 15 using pivaloylchloride (0.9 g) instead of p-anisoyl-chloride and is recrystallized from m-hexane. Yield: 1.6 g; m.p.: 105°-7° C.

EXAMPLE 38

N-Isobutyroyl-3-(3,3-dimethyl-tetrahydro-1,4-thiazin-4-yl)-sydnone imine

The compound is obtained analogously to Example 15 using isobutyroylchloride (0.9 g) instead of p-anisoyl-chloride and is recrysallized from diisopropylether. Yield: 1.4 g; m.p.: 119°-121° C.

Pharmaceutical preparations are described in the following Examples A to F:

EXAMPLE A

Soft gelatin capsules containing 5 mg of active compound per capsule:

|  | per capsule |
|---|---|
| Active compound | 5 mg |
| Fractionated triglyceride mixture from coconut fat | 150 mg |
| Capsule content | 155 mg |

EXAMPLE B

Injection solution containing 1 mg of active compound per ml:

|  | per ml |
|---|---|
| Active compound | 1.0 mg |
| Polyethylene glycol 400 | 0.3 ml |
| Sodium chloride | 2.7 mg |
| Water for injection purposes to | 1 ml |

EXAMPLE C

Emulsion containing 3 mg of active compound per 5 ml

|  | per 100 ml of emulsion |
|---|---|
| Active compound | 0.06 g |
| Neutral oil | q.s. |
| Sodium carboxymethyl cellulose | 0.6 g |
| Polyoxyethylene stearate | q.s. |
| Glycerol, pure | 0.2 to 2.0 g |
| Flavouring | q.s. |
| Water (demineralized or distilled) to | 100 ml |

EXAMPLE D

Rectal medicament containing 4 mg of active compound per suppository

|  | per suppository |
|---|---|
| Active compound | 4 mg |
| Suppository foundation to | 2 g |

EXAMPLE E

Tablets containing 2 mg of active compound per tablet

|  | per tablet |
|---|---|
| Active compound | 2 mg |
| Lactose | 60 mg |
| Maize starch | 30 mg |
| Soluble starch | 4 mg |
| Magnesium stearate | 4 mg |
|  | 100 mg |

EXAMPLE F

Coated tablets containing 1 mg of active compound per coated tablet

|  | per coated tablet |
|---|---|
| Active compound | 1 mg |
| Maize starch | 100 mg |
| Lactose | 60 mg |
| Sec. calcium phosphate | 30 mg |

| | per coated tablet |
|---|---|
| Soluble starch | 3 mg |
| Magnesium stearate | 2 mg |
| Colloidal silica | 4 mg |
| | 200 mg |

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

What is claimed is:

1. Substituted 3-aminosydnone imines of the general formula I

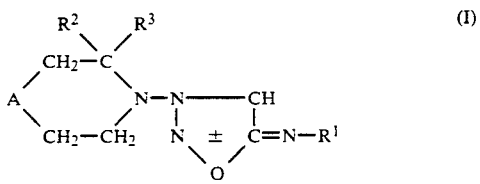

and their pharmacologically acceptable acid addition salts, in which

A denotes the radical —$CH_2$—, —O—, —$S(O_n)$—, —$N(R^4)$— or a direct bond;

$R^1$ denotes hydrogen or the radical —$COR^5$, $R^2$, $R^3$ denote alkyl having 1 to 4 C atoms $R^4$ denotes alkyl having 1 to 4 C atoms; hydroxyalkyl having 2 to 4 C atoms; phenylalkyl having 1 to 4 C atoms in the alkyl radical;

$R^5$ denotes an aliphatic radical having 1 to 4 C atoms which may also be substituted by alkoxy having 1 to 3 C atoms; a cycloaliphatic radical having 5 to 7 C atoms; a bicycloaliphatic radical having 7 to 14 C atoms; a tricycloaliphatic radical having 7 to 16 C atoms; an alkoxy radical having 1 to 6 C atoms; an aryloxy radical having 6 to 10 C atoms; an alkoxycarbonyl radical having a total of 2 to 7 C atoms; an aryl radical having 6 to 10 C atoms; an aryl radical having 6 to 10 C atoms which is mono-, di- or trisubstituted by 1 to 3 halogen atoms or by 1 to 3 alkyl radicals having 1 to 3 C atoms or by 1 to 3 alkoxy radicals having 1 to 3 C atoms or by 1 or 2 nitro groups;

n denotes the number 0, 1 or 2.

2. Substituted 3-aminosydnone imines according to claim 1, characterized in that $R^2$ and $R^3$ denote methyl.

3. Substituted 3-aminosydnone imines according to claim 1, characterized in that $R^1$ denotes hydrogen.

4. Substituted 3-aminosydnone imines according to claim 1, characterized in that $R^1$ is selected from the group consisting of —$COR^5$ and $R^5$ denotes methyl, ethyl, isopropyl, tert.-butyl, methoxy, ethoxy, isopropoxy, cyclohexyl, phenyl or 4-chlorophenyl.

5. Substituted 3-aminosydnone imines according to claim 1, characterized in that A denotes —$CH_2$—, —O— or —$N(R^4)$—.

6. 3-(3,3-Dimethylmorpholin-4-yl)-sydnone imine and its pharmacologically acceptable acid addition salts.

7. 3-(2,2-Dimethylpiperidin-1-yl)-sydnone imines and its pharmacologically acceptable acid addition salts.

8. 3-(4-Isopropyl-2,2-dimethyl-piperazin-1-yl)-sydnone imine and its pharmacologically acceptable acid addition salts.

9. Method for treating disorders of the cardiovascular system, which comprises administering an effective dose of a compound of claim 1 to a patient in need thereof.

10. Pharmaceutical composition containing a compound of claim 1 or an acid addition salt thereof as the active ingredient together with pharmaceutically acceptable excipients and additives.

11. N-Ethoxycarbonyl-3-(2,2-dimethylpiperidin-1-yl)sydnone imine and its pharmacologically acceptable acid addition salts.

12. N-Cyclohexylcarbonyl-3-(3,3-dimethylmorpholin-4-yl)sydnone imine and its pharmacologically acceptable acid addition salts.

13. N-Isobutyroyl-3-(2,2-dimethyl-4-isopropyl-piperazin-1-yl)-sydnone imine and its pharmacologically acceptable acid addition salts.

14. 3-(3,3-Dimethyl-tetrahydro-1.4-thiazin-4-yl)sydnone imine-hydrochloride.

15. 3-(3,3-Dimethyl-1.1-dioxo-tetrahydro-1.4-thiazin-4-yl)-sydnone imine-hydrochloride.

16. 3-(3,3-Dimethyl-1-oxo-tetrahydro-1.4-thiazin-4-yl)sydnone imine-hydrochloride.

* * * * *